United States Patent [19]

Barmby

[11] 4,344,424

[45] Aug. 17, 1982

[54] ANTI-EATING FACE MASK

[76] Inventor: Lucy L. Barmby, 9550 Jackson Rd., Sacramento, Calif. 95826

[21] Appl. No.: 134,557

[22] Filed: Mar. 27, 1980

[51] Int. Cl.³ .............................................. A61F 5/56
[52] U.S. Cl. .................................................. 128/136
[58] Field of Search ...................... 128/133, 136, 137

[56] References Cited

U.S. PATENT DOCUMENTS

| | | | |
|---|---|---|---|
| 853,025 | 5/1907 | McCalmont | 128/133 |
| 1,297,842 | 3/1919 | Harllee | 128/136 |
| 1,629,892 | 5/1927 | Storms | 128/136 |
| 2,276,612 | 3/1942 | Ellis | 128/136 |
| 3,189,073 | 6/1965 | Todd | 128/133 |
| 3,818,906 | 6/1974 | Stubbs | 128/136 |

*Primary Examiner*—Kyle L. Howell
*Assistant Examiner*—C. W. Shedd
*Attorney, Agent, or Firm*—Blair, Brown & Kreten

[57] ABSTRACT

An anti-eating face mask which includes a cup-shaped member conforming to the shape of the mouth and chin area of the user, together with a hoop member and straps detachably engageable with a user's head for mounting the cup-shaped member in overlying relationship with the user's mouth and chin area under the nose thereby preventing the ingestion of food by the user.

2 Claims, 3 Drawing Figures

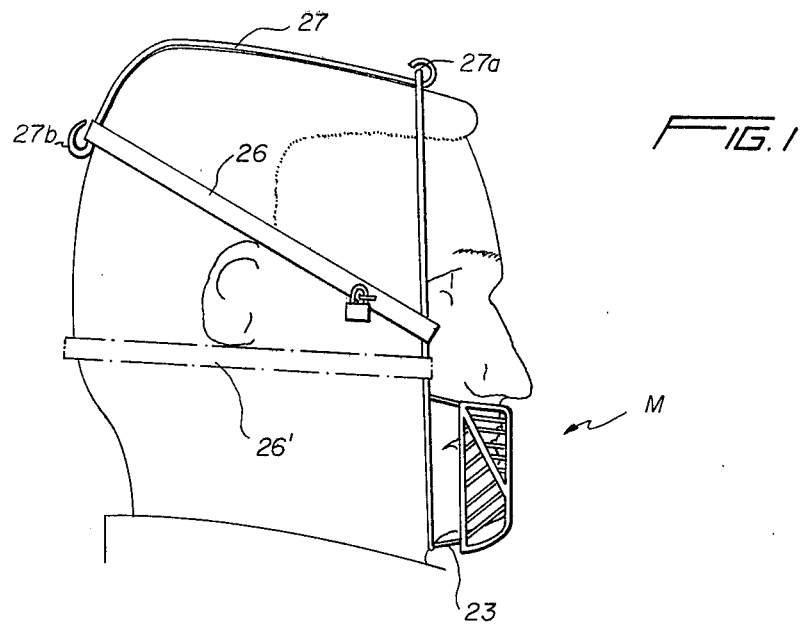
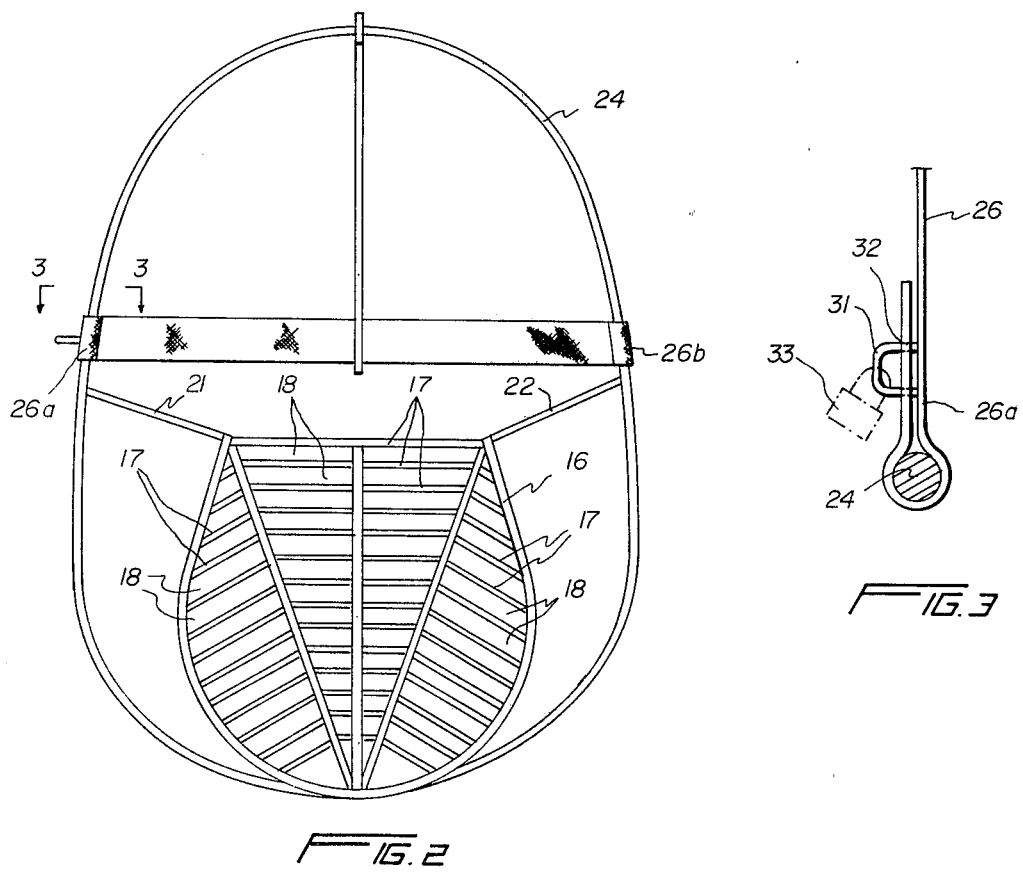

ANTI-EATING FACE MASK

BACKGROUND OF THE INVENTION

Obesity is a basic problem with which many people today are confronted and, as clearly indicated by the variety of diets proposed to conquer overweight, the major contributing factor to overweight is the excessive consumption of food. The temptation to eat which leads one to eat excessively is ever present and the ready availability of attractively prepared, taste-tempting foods makes the temptation to eat and therefore to over-eat virtually irresistible. Frequently, this temptation is so great that compulsive eating is not uncommon and many persons are virtually without the strength of will to resist overeating. The average person, therefore, does have a problem as to the over consumption of food but, even worse, when certain individuals are exposed to food constantly such as chefs, cooks, restaurant personnel or the like, it is a foregone conclusion that these individuals will consume far more food than is proper particularly when such food is usually readily available at no cost. Typical of such groups of individuals is the housewife who must frequently cook meals during the day which generally includes the preparation of such fattening foods such as pies, pastries, and the like. During the preparation of such meals not only is there the temptation to nibble on the food being prepared but it is generally necessary that the food be tasted during preparation thereby constantly stimulating the appetite and promoting the consumption of large quantities of food.

OBJECTS AND SUMMARY OF THE INVENTION

Accordingly, a primary object of this invention is to provide a new and novel device for preventing the consumption of food by an individual.

Another object of this invention is to provide a new and novel mask which is worn on the head of a user to prevent the consumption of food by the user and therefore an attendant overweight problem.

A further object of this invention is to provide a new and novel device which may be easily attached to the head of the user in a detachable manner for encompassing the mouth area of the user thereby preventing food from being ingested by the user.

Still another object of this invention is to provide a new and novel device which is worn on the head of the user for preventing the ingestion of food, which is simple and inexpensive in construction, which does not interfere with transmission of speech or breathing by the user and which may be locked in place on the user's head to prevent removal while at the same time permitting removal under emergency conditions.

A still further object of this invention is to provide a new and novel device for preventing the ingestion of food by a user which is useful in the prevention of overweight, which may be used in the medical profession to prevent food consumption during the period before an operation, which may be made in any suitable size and which may also be used to prevent the smoking of cigarettes and the like.

The objects stated above and other related objects are accomplished by the provision of a cup-shaped member conforming generally to the shape of the mouth and chin area of a user's face below the nose. The cup-shaped member is provided with mounting means engageable with the head of a user which permits the member to be positioned in overlying relationship with the mouth and chin area of the user's face so that ingestion of food by the user is prevented.

Other objects and advantages will become apparent when viewed in the light of the following description taken in connection with the accompanying drawing.

BRIEF DESCRIPTION OF THE DRAWING

FIG. 1 is a profile view of a user's head showing the anti-eating face mask of the invention in an installed position;

FIG. 2 is an enlarged front view of the face mask of FIG. 1; and

FIG. 3 is an enlarged sectional view taken substantially along 3—3 of FIG. 2 in the direction of the arrows.

DESCRIPTION OF THE PREFERRED EMBODIMENT

Referring now to the drawings there is shown the anti-eating face mask of the invention which is designated generally by the letter M. The face mask M is shown in the installed position on the face of a user's head in FIG. 1 and includes a cup-shaped member 16 of rigid material such as wire or the like which conforms generally to the mouth and chin area of a user's face below the nose. In the illustrated embodiment, the cup-shaped member 16 is formed from a plurality of wires 17 which are arranged as shown best in FIG. 2 in a unitary construction to define openings 18 therebetween. The openings 18 are of a size to permit speech plus, at the same time, prevent the ingress of food into the mouth of the user.

Means engagable with the user's head are provided on the mask M for detachably mounting the cup-shaped member 16 in overlying relationship with the user's mouth and chin area. More specifically, the cup-shaped member 16 is secured by means of rods or wires 21–23 to a hoop member 24 which is arranged to encircle the user's head extending around the top of the head, the side areas of the face and under the chin. Rods 21, 22 extend outwardly on opposite sides of the cup-shaped member 16 and are attached at the outer ends to the hoop member 24, rod 23 extending between the bottom of the cup-shaped member 16 to the lower portion of the hoop member 24, as shown in FIG. 1, thereby providing a rigid construction comprising the hoop member 24 and the cup-shaped member 16.

The mounting means of the invention also includes a flexible strap 26 having end portions 26a, 26b attached to the hoop member 24. The mounting means also include a strap member 27 connected at one end 27a to the top of the hoop member 24 and at the other end 27b to the flexible strap 26 intermediate the ends 26a, 26b. In the illustrated embodiment, both straps 26, 27 are preferably formed from leather. The end 26b of flexible strap 26 may be attached in any suitable manner permanently to the hoop member 24 as shown in FIG. 2 and the other end portion 26a of the strap 26 is preferably releasably attached to the hoop member 24 as shown best in FIG. 3.

As shown in FIG. 3, the end portion 26a of strap 26 is provided with a staple 31 suitably secured thereto and a slotted aperture 32, longitudinally spaced from the staple 31, for accommodating the staple 31. Thus, the strap end portion 26a is arranged to be formed into a loop around the hoop member 24 and the staple 31 inserted into the slotted aperture 32 so as to extend outwardly from the strap end portion 26a. In the preferred embodiment, locking means are included with the mounting means of the invention which includes any conventional lock 33 of the type using a key which lock is engageable with the staple 31 in the position shown in FIG. 3 so as to lock the end portion 26a of the strap 26 on the hoop 24 preventing its removal. However, under emergency conditions, the strap 26 may be cut and the face mask M of the invention removed.

In the illustrated embodiment, the strap 26 is shown extending over the user's ear but it should be understood that, if desired, the strap 26 may be positioned below the user's ear as shown in broken lines and as indicated by the reference numeral 26'. The strap member 27 is extended in length accordingly to connect the end 27b with the strap 26'.

Having thus described the preferred embodiment of the invention it should be understood that numerous structural modifications and adaptations may be resorted to without departing from the spirit of the invention.

What is claimed is:

1. A face mask for preventing the introduction of substances into the mouth of the wearer comprising in combination;

a cup shaped member conforming generally to the shape of the mouth and chin area of the wearer's face below the nose, said cup shaped member formed of rigid material with openings to allow breathing therethrough, means for mounting said cup shaped member over the mouth including plural straps extending from said cup over the head of the wearer, one of said straps provided with a means for separation to allow for placement and removal of said face mask, and a lock at said separation means to prevent removal of said face mask, said mounting means further including a hoop member of rigid material adapted to extend over the user's head and chin and a flexible strap having end portions connected to said hoop member for extending around the back of the user's head and a strap member adapted to extend over the top of the user's head, said strap member being connected at opposite ends to said hoop member and to said strap intermediate the ends of said strap, said separation means including a staple adjacent one end portion of said strap, and an aperture in said strap one end portion in longitudinally spaced relationship with said staple, said strap one end portion arranged to be looped around said hoop member for insertion of said staple in said aperture and said lock engageable with said staple extending through said aperture for locking said strap one end portion to said hoop member, wherein said hoop member is attached to said cup shaped member by plural rods extending therebetween, two of said rods attached to opposed sides of said cup shaped member, a third said rod attached to a lowermost portion of said hoop member.

2. A face mask in accordance with claim 1 wherein said cup-shaped member comprises a screen formed of a plurality of wires, said wires in said screen defining said openings therebetween.

* * * * *